US006802190B2

(12) United States Patent
Reed et al.

(10) Patent No.: US 6,802,190 B2
(45) Date of Patent: Oct. 12, 2004

(54) METHOD OF FABRICATING A GRIN FIBER (75) Inventors: William Alfred Reed, Summit, NJ (US); Mark J Schnitzer, Summit, NJ (US)

(73) Assignee: Lucent Technologies Inc., Murray Hill, NJ (US)

(*) Notice: Subject to any disclaimer, the term of this patent is extended or adjusted under 35 U.S.C. 154(b) by 0 days.

(21) Appl. No.: 10/316,505

(22) Filed: Dec. 11, 2002

(65) Prior Publication Data

US 2003/0118305 A1 Jun. 26, 2003

Related U.S. Application Data

(62) Division of application No. 09/896,777, filed on Jun. 29, 2001, now Pat. No. 6,542,665.
(60) Provisional application No. 60/292,017, filed on May 19, 2001, and provisional application No. 60/269,586, filed on Feb. 17, 2001.

(51) Int. Cl.[7] ............................................. C03B 37/027
(52) U.S. Cl. ............................. 65/377; 65/387; 65/421; 65/429; 65/407
(58) Field of Search .......................... 65/377, 387, 421, 65/429, 407

(56) References Cited

U.S. PATENT DOCUMENTS

| | | | |
|---|---|---|---|
| 4,217,027 A | 8/1980 | MacChesney et al. | 350/96.3 |
| 4,262,035 A | 4/1981 | Jaeger et al. | 427/39 |
| RE30,635 E | * 6/1981 | Kuppers et al. | 427/573 |
| 4,701,011 A | * 10/1987 | Emkey et al. | 385/34 |
| 4,793,843 A | * 12/1988 | Pluijms et al. | 65/397 |
| 4,900,120 A | 2/1990 | Caviglia et al. | 350/96.18 |
| 4,909,816 A | 3/1990 | MacChesney et al. | 65/3.12 |
| 5,000,771 A | * 3/1991 | Fleming et al. | 65/391 |
| 5,050,954 A | 9/1991 | Gardner et al. | 385/16 |
| 5,076,672 A | 12/1991 | Tsuda et al. | 359/244 |
| 5,321,501 A | 6/1994 | Swanson et al. | 356/345 |
| 5,337,380 A | 8/1994 | Darbon et al. | 385/28 |
| 5,384,874 A | 1/1995 | Hirai et al. | 385/34 |
| 5,680,237 A | 10/1997 | Cheng | 359/131 |
| 5,865,867 A | 2/1999 | Kinoshita | 65/17.3 |
| 5,881,195 A | 3/1999 | Walker | 385/116 |

(List continued on next page.)

FOREIGN PATENT DOCUMENTS

| | | | |
|---|---|---|---|
| EP | 0972752 A1 | 1/2000 | C03B/37/018 |
| EP | 1035083 A1 | 9/2000 | C03B/37/018 |
| SE | 512393 | 6/1994 | G02B/6/28 |
| WO | WO 10/11409 A2 | 2/2001 | G02B/23/24 |

OTHER PUBLICATIONS

U.S. patent application Ser. No. 09/896,789, Reed et al., filed Jan. 29, 2001.
U.S. patent application Ser. No. 09/919,017, Reed et al., filed Jul. 31, 2001.
U.S. patent application Ser. No. 09/922,659, Fee et al., filed Aug. 6, 2001.
Emkey, W.L., et al., IEEE, "*Analysis and Evaluation of Graded–Index Fiber–Lenses,*" vol. 5, No. 9, pp. 1156–1164, Sep. 1987.
Chanciou, P., et al., "*Expanded Single Mode Fiber,*" WDD4, 2000, 3 pages.

(List continued on next page.)

*Primary Examiner*—John Hoffmann
(74) *Attorney, Agent, or Firm*—John F. McCabe (57) ABSTRACT

A method for fabricating a GRIN fiber includes forming a tube of silica-glass having a tubular core and a concentric tubular cladding adjacent and external to the tubular core. The core has a dopant density with a radially graded profile. The method includes partially collapsing the tube by applying heat thereto. The partially collapsed tube has a central channel. The method includes passing a glass etchant through the central canal to remove an internal layer of silica glass, and then, collapsing the etched tube to a rod-like preform.

9 Claims, 8 Drawing Sheets

U.S. PATENT DOCUMENTS

| | | | |
|---|---|---|---|
| 5,905,838 A | 5/1999 | Judy et al. | 385/123 |
| 5,910,839 A | 6/1999 | Erskine | 356/345 |
| 5,956,355 A | 9/1999 | Swanson et al. | 372/20 |
| 6,014,483 A | 1/2000 | Thual et al. | 385/33 |
| 6,105,396 A | 8/2000 | Glodis et al. | 65/377 |
| 6,131,413 A | 10/2000 | Rousseau et al. | 65/377 |
| 6,134,003 A | 10/2000 | Tearney et al. | 356/345 |
| 6,172,817 B1 | 1/2001 | Senapati et al. | 359/654 |
| 6,174,828 B1 | 1/2001 | Morita et al. | 501/12 |
| 6,219,477 B1 | 4/2001 | Peck, Jr. | 385/34 |
| 6,267,915 B1 | 7/2001 | Park et al. | 264/1.24 |
| 6,445,939 B1 * | 9/2002 | Swanson et al. | 600/342 |

OTHER PUBLICATIONS

A Product Announcement of ENST Bretagne, Chanciou, P., et al., "*Expanded Single Mode Fiber*," 2–pages, Mar. 2001.

European Patent Search Report, Application No. 01310121.7–2205, Munich, Mar. 3, 2002.

Patent Abstracts of Japan Publication No. 60166244, "*Manufacture of Optical Fiber Preform*" by Okamura Koji (Published on Aug. 29, 1985, by Japanese Patent Office) 1 page.

Shiraishi, K., et al., "*Spotsize Contracation in Standard Single–Mode Fibers by Use of a GI–Fiber Tip with a High Focusing Parameter*," IEEE Photonics Technology Letters, vol. 10, No. 12, Dec. 1998, pp. 1757–1759.

European Patent Search Report, Application No. 01310121.7–2205, Munich, Mar. 26, 2002.

* cited by examiner

METHOD OF FABRICATING A GRIN FIBER

This is a divisional of application Ser. No. 09/896,777 filed on Jun. 29, 2001 now U.S. Pat. No. 6,542,665.

This application claims the benefit of U.S. Provisional Patent Application No. 60/269,586, filed Feb. 17, 2001, and of U.S. Provisional Application No. 60/292,017, filed May 19, 2001.

BACKGROUND OF THE INVENTION

1. Field of the Invention

This invention relates to optical devices and graded refractive index lenses.

2. Discussion of the Related Art

A graded refractive index (GRIN) lens has a refractive index whose value varies with radial distance from the axis of the lens. The non-trivial variation in refractive index causes light refraction and gives the GRIN lens focussing capabilities that are similar to those of an ordinary lens. Therefore, many optical devices employ GRIN or ordinary lenses interchangeably.

Figure 1:
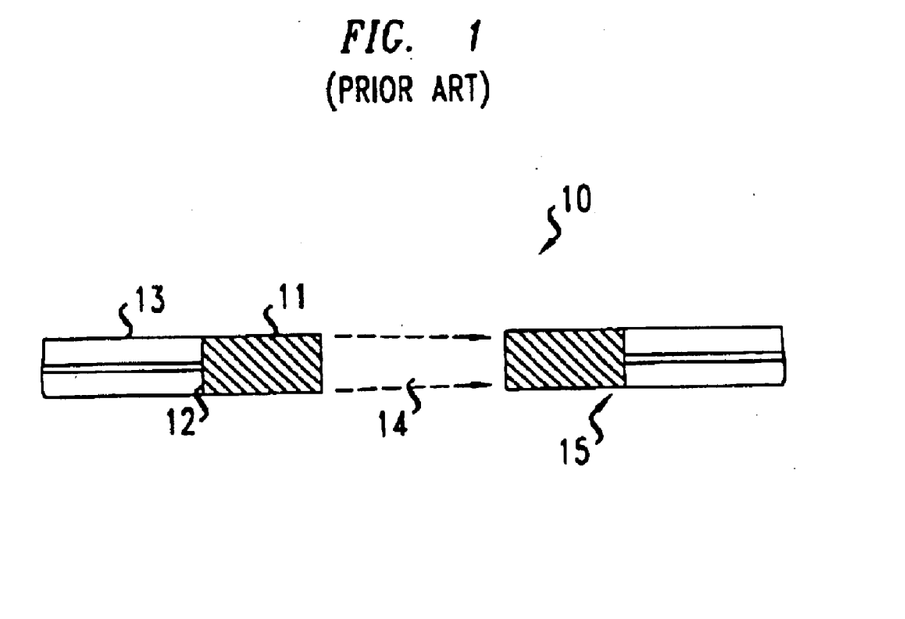
FIG. 1 is a cross-sectional view of a fiber device that uses a conventional GRIN fiber lens to end-couple two optical fibers.

Many optical devices use lenses to focus, collimate, or expand light beams. FIG. 1 shows a fiber device 10 in which a GRIN fiber lens 11 is fused to a terminal end 12 of an optical fiber 13. The GRIN fiber lens 11 expands and collimates the light beam emitted by the optical fiber 13. The GRIN fiber lens 11 improves the optical coupling between optical fiber 13 and fiber device 15 as compared to the coupling that would otherwise exist between the fiber 13 and device 15 due to diffraction. The GRIN fiber lens 11 reduces diffraction losses when the optical fiber 13 is optically coupled to another optical fiber.

Since the diameter of a light beam varies along the axis of a GRIN lens, the beam diameter variations provide a measure of the lens' length. The length over which the variations in the beam diameter make two complete cycles is known as the pitch of the lens. Typically, lengths of GRIN lens are referred to in multiples of the pitch length, e.g., ½ pitch or ¼ pitch.

BRIEF SUMMARY OF THE INVENTION

Some optical devices embodying principles of the inventions include a GRIN fiber lens in which the refractive index has a new radial profile. When attached to an end of an optical fiber, the new GRIN fiber lens increases the Rayleigh range of the emitted beam above that of a light beam emitted by a similar fiber attached to a conventional GRIN lens. The increased Rayleigh range improves beam collimation so that the fiber may couple to other optical devices over larger distance ranges.

In first aspect, the invention features a method for fabricating a GRIN fiber. The method includes providing a doped silica-glass preform having an axial core and a tubular cladding surrounding and adjacent the core. The core has a graded index of refraction. The cladding has a lower refractive index than the core. The method includes etching the preform to remove an outer layer of the tubular cladding and drawing the GRIN fiber from the etched preform.

In a second aspect, the invention features another method for fabricating a GRIN fiber. The method includes forming a tube of silica-glass having a tubular core and a concentric tubular cladding adjacent and external to the tubular core. The core has a dopant density with a radially graded profile. The method also includes partially collapsing the tube by applying heat thereto. The partially collapsed tube has a central channel. The method includes passing a glass etchant through the central canal to remove an internal layer of silica glass, and then, collapsing the etched tube to a rod-like preform.

BRIEF DESCRIPTION OF THE FIGURES

In the Figures, like reference numbers refer to functionally similar features.

DETAILED DESCRIPTION OF THE EMBODIMENTS

1. Grin Fiber Lenses

Figure 2:
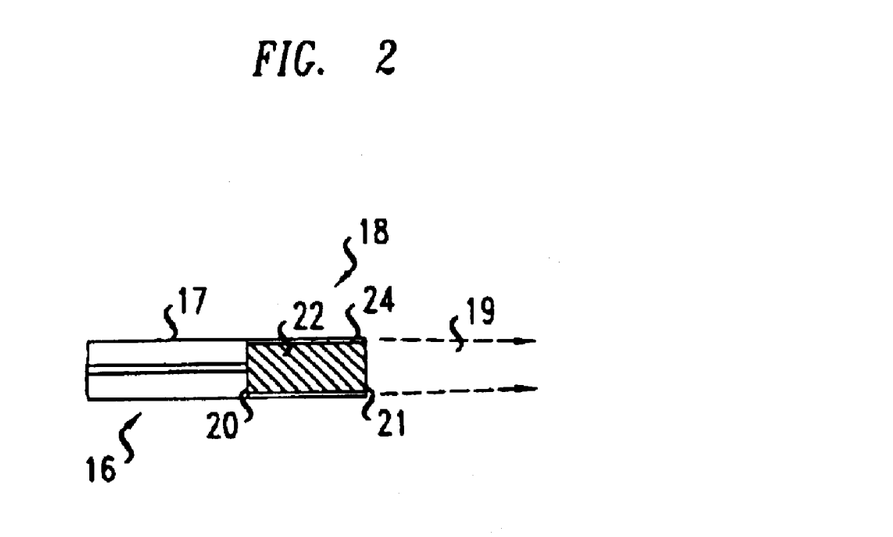
FIG. 2 is a cross-sectional view of a fiber device in which an optical fiber is fused to an embodiment of a GRIN fiber lens.

FIG. 2 shows an optical fiber device 16 in which an optical fiber 17 is end-coupled to a GRIN fiber lens 18, e.g., fused or glued to the fiber 17. The GRIN fiber lens 18 and optical fiber 17 are co-axial and have similar or equal outer diameters whose values are in the range of about 100 μm to about 135 μm, e.g., 125 μm. The GRIN fiber lens 18 collimates a light beam 19 emitted from the end of the optical fiber 17 thereby decreasing the numerical aperture below that of a bare optical fiber. The GRIN fiber lens 18 is also able to focus an incident light beam into the end 20 of the optical fiber 17.

Exemplary optical fibers 17 include single-mode and multi-mode fibers.

Exemplary GRIN fiber lenses 18 have refractive indexes whose radial profiles differ significantly from those of conventional GRIN fiber lenses. The new radial profiles enable decreased numerical apertures and increased Rayleigh ranges for fiber device 16 as compared to values of the same quantities in conventional fiber device 10 of FIG. 1. The decreased numerical aperture implies that an appropriate length GRIN fiber lens 18 would cause less diffraction and a lower power density in emitted light beam 19 than in the light beam 14 emitted by conventional fiber device 10.

The increased Rayleigh range implies that emitted beam 19 is better collimated than the beam 14. The improved properties of the emitted beam 19 facilitate transverse alignments required to end-couple the fiber device 16 to another fiber device (not shown).

In some embodiments of fiber device 16, GRIN fiber lens 18 has an end face 21 that is angle cleaved to reduce back reflections of light into optical fiber 17. In particular, a normal vector to the end-face 21 is preferably cleaved at an angle 1°–2° or less with respect to the axis of the GRIN fiber lens 18. This cleave angle is smaller than a typical cleave angle of about 8° used to lower reflections from its end face back into the optical fiber (not shown). The beam expansion provided by the GRIN fiber lens 18 lowers the amount of angle cleave needed to produce an equivalent reduction in back reflections into the fiber 17.

The new GRIN fiber lens 18 has a circular core 22 and an annular cladding 24 that surrounds the core 22. In the core 22, the refractive index varies with the radial distance from the axis of the GRIN fiber lens 18. In the cladding 24, the refractive index is constant and has a lower value than in the core 22. The GRIN fiber lens has an outer diameter of about 125 μm. The outer diameter is the same as that of conventional GRIN fiber lens 11 shown in FIG. 1. But, the new and conventional GRIN fiber lenses 11, 18 have different radial refractive index profiles due to differences in density distributions of dopant atoms in their cores. Exemplary dopants include germanium (Ge), aluminum (Al), phosphorus (P), and fluorine (F).

Figure 3A:
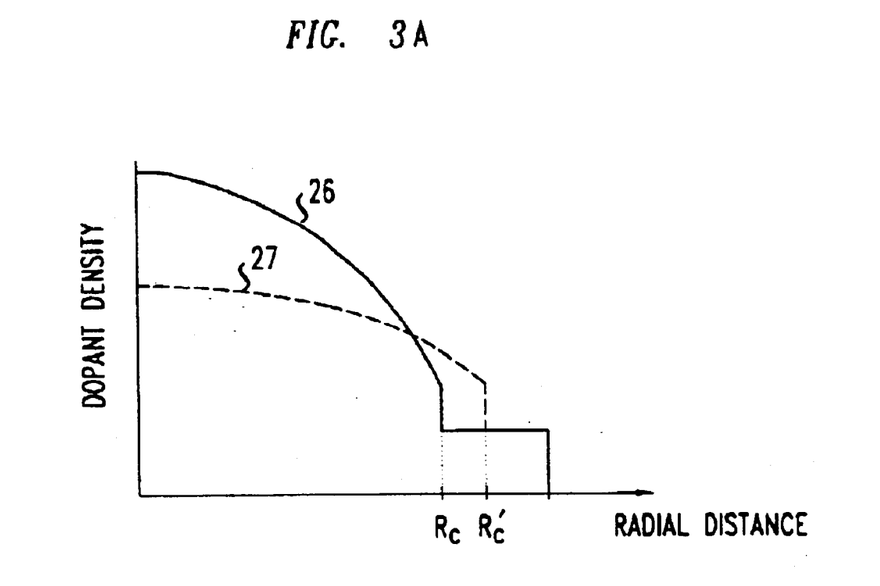
FIG. 3A shows radial profiles of germanium dopant densities in a conventional GRIN fiber lens and a new GRIN fiber lens.

FIG. 3A shows radial profiles 26 and 27 of Ge-dopant densities in conventional GRIN fiber lens 11 and new GRIN fiber lens 18, respectively. In the core 22 of the new GRIN fiber lens 18, the Ge-dopant density has a radial profile that is largest on the central axis and curved concave downwards. The profile does not have an axial density dip, i.e., unlike some conventional GRIN fiber lenses (not shown). The curvature of the radial profile of the Ge-dopant has a smaller average magnitude in the core 22 of the new GRIN fiber lens 18 than in the core of conventional GRIN fiber lens 11. In the claddings of both the new and conventional GRIN fiber lenses 18, 11, the Ge-dopant densities are lower than in the fiber cores and are constant with respect to radial distance from the fiber axes.

The boundaries between core and cladding, i.e., at radial distances of $R_c$ and $R_c'$, are characterized by abrupt changes in the Ge-dopant densities and/or radial gradients of the densities. The core diameter is larger in the new GRIN fiber lens 18 than in conventional GRIN fiber lens 11, i.e., $R_c' > R_c$. Increasing the core diameter increases the Rayleigh range of fiber device 16 when a GRIN fiber lens 18 of appropriate length is used therein. Exemplary embodiments of the GRIN fiber lens 18 have an outer diameter of about 125 μm. and a core 22 with a diameter of about 85 μm, preferably 100 μm or more, and more preferably 105 μm or more. In some GRIN fiber lenses 18, cladding is absent so that the core has a diameter of about 125 μm.

Figure 3B:
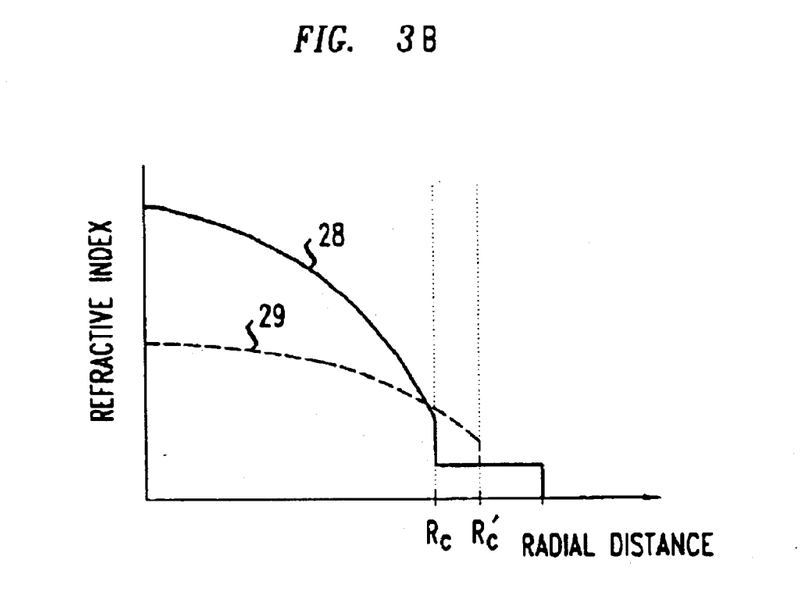
FIG. 3B shows radial profiles of refractive indexes for the GRIN fiber lenses of FIG. 3A.

FIG. 3B shows refractive index profiles 28 and 29 that correspond to the Ge-dopant density profiles 26 and 27 of GRIN fiber lenses 11 and 18, respectively. The radial profiles 28, 29 are concave down in the core 22.

The radial profiles 28, 29 also show that the new GRIN fiber lens 18 has a refractive index whose radial profile has a significantly more gentle variation than in the conventional GRIN fiber lens 11. A parameter "g" measures the radial curvature of the refractive index profile in the core of a GRIN fiber lens. In particular, the parameter g is defined as:

$$g = -\frac{1}{n_0} \frac{d^2 P(r)}{dr^2}\bigg|_{r=0}$$

Here, "r" is radial distance for the axis of the GRIN fiber lens, no is the value of the refractive index on the axis of the GRIN fiber lens, and P(r) is the value of the refractive index at the distance "r" from the axis of the fiber lens. The GRIN fiber lens 18 has a refractive index profile that has a gentler radial variation over the lens' core. Refractive index profiles of the GRIN fiber lens 18 typically, have radial curvatures that are smaller in magnitude than those disclosed in Table 1 of "Analysis and Evaluation of Graded-Index Fiber-Lenses", Journal of Lightwave Technology, Vol. LT-5, No. 9 (September 1987), pages 1156–1164, by W. L. Emkey et al (EMKEY), which is incorporated by reference herein in its entirety. Typically, magnitudes of the radial curvature of refractive index profile for embodiments of the GRIN fiber lens 18 are, at least, twice as small as values for the same quantity that are disclosed in EMKEY. Exemplary GRIN fiber lens 18 have a "g" that is less than $1.7 \times 10^{-6}$ μm$^{-2}$, preferable less than about $0.9 \times 10^{-6}$ m$^{-2}$ and more preferably less than about $5.0 \times 10^{-7}$ μm$^{-2}$. For 125 μm—diameter GRIN fiber lenses 18, values of "g" are selected from the range $1.7 \times 10^{-6}$ μm$^{-2}$ to $5.0 \times 10^{-7}$ μm$^{-2}$ and preferably in the range $0.9 \times 10^{-6}$ μm$^{-2}$ to $5.0 \times 10^{-7}$ μm$^{-2}$ to provide good beam collimation.

Exemplary GRIN fiber lens 18 have core index profiles that vary approximately quadratically in the distance from the lens axis. But, other embodiments of the GRIN fiber lens 18 have non-quadratic index profiles.

Referring again to FIG. 2, the new GRIN fiber lens 18 has a wider core 22 than the conventional GRIN fiber lens 11. The wider core 22 and the smaller value of the parameter "g" enable the new GRIN fiber lens 18 of appropriate length to produce a beam with a wider cross section and a lower energy density when used as a beam collimator.

Figure 4A:
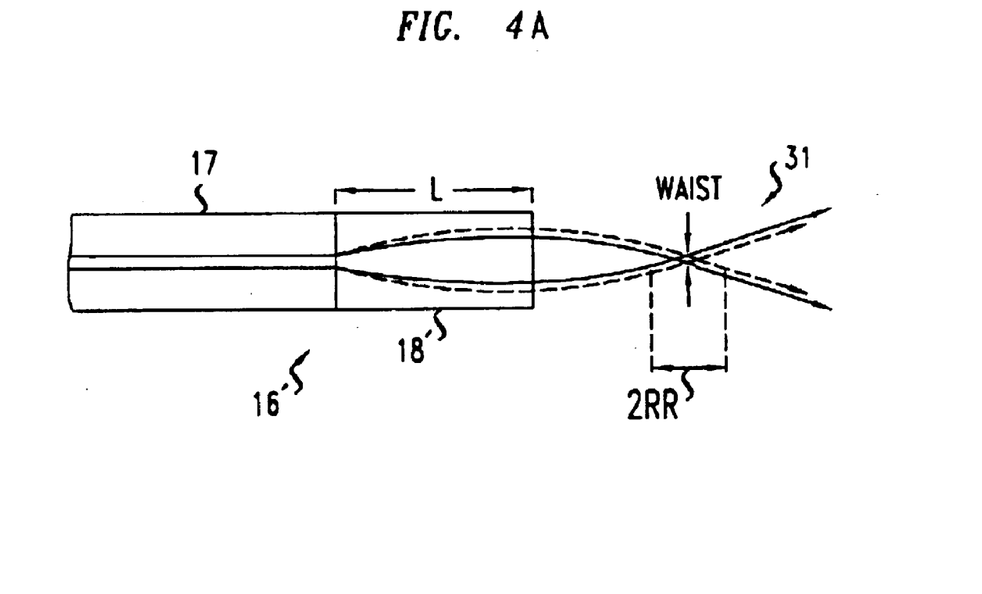
FIGS. 4A and 4B illustrate beam collimation in fiber devices with new and conventional GRIN fiber lenses, respectively.
Figure 4B:
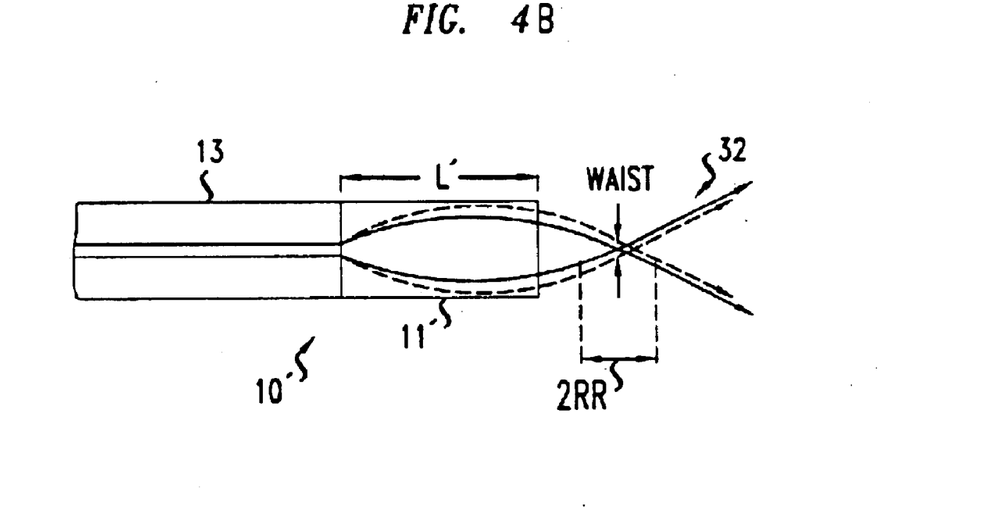

FIGS. 4A and 4B show light beams 31, 32 emitted by new and conventional fiber devices 16', 10' of the types shown in FIGS. 1 and 2. The fiber devices 16', 10' have GRIN fiber lenses 18', 11' with equal pitches, e.g., 5/16 pitch, but different refractive index profiles. The new profile in the lens 18' significantly increases the Rayleigh range, RR, of the fiber device 16' above the Rayleigh range, RR', of the conventional device 10'. The increased Rayleigh range results from a more gradual beam expansion in the GRIN fiber lens 18' as compared to the beam expansion in the conventional GRIN fiber lens 11. In particular, FIGS. 4A and 4B show that making the radial curvature in refractive index of a GRIN fiber lens smaller than in conventional GRIN fiber lenses significantly reduces the divergence of the emitted beam for a given pitch.

The Rayleigh range determines the distance range over which an optical device can couple to a fiber device without substantial losses. The larger Rayleigh range in the new fiber device 16' makes a larger set of distances available for end-coupling to such a device than are available for the conventional fiber device 10'.

GRIN lenses of equal pitch ordinarily have equal products of $g^{1/2}$ times the lens-length. Since the new GRIN fiber lenses 18 have smaller g-values, the new GRIN fiber lenses 18 are ordinarily longer than conventional GRIN fiber lenses 11 of equal pitch. The longer lengths make the new GRIN fiber lenses 18 easier to handle, align, and fuse to optical fibers than the conventional GRIN fiber lenses 11. The increased lengths also reduce collimation errors associated with cleaving errors that occur during production of the new GRIN fiber lenses 18.

Figure 5:
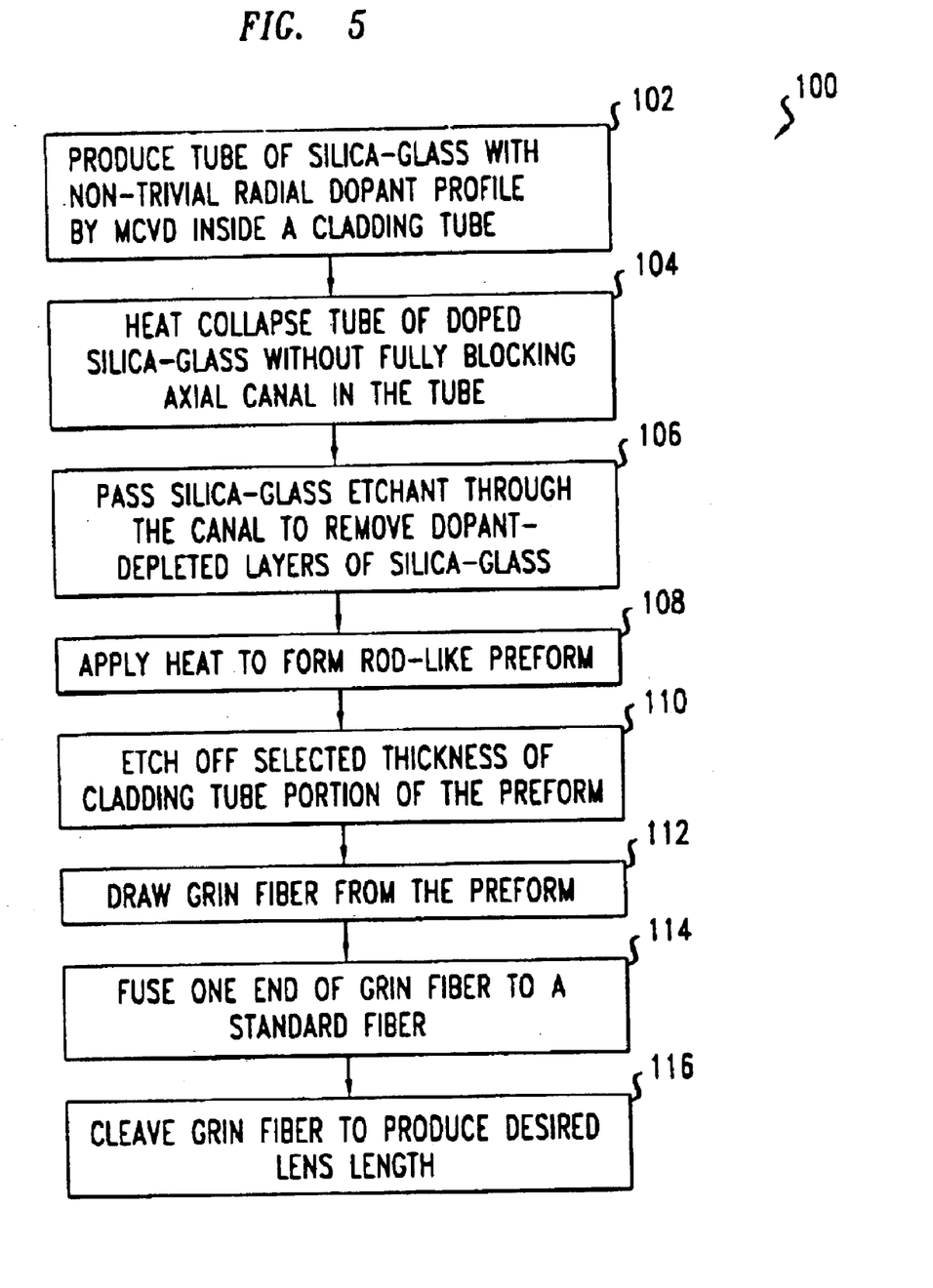
FIG. 5 is a flow chart for a method of fabricating the fiber device of FIG. 2.

FIG. 5 is a flow chart for a method 100 of fabricating a GRIN fiber lens of doped silica-glass through modified chemical vapor deposition (MCVD). MCVD construction of optical fibers is described in U.S. Pat. Nos. 4,909,816 and 4,217,027, which are incorporated herein by reference in their entirety. The fabrication method 100 includes forming an improved GRIN preform and then, using the improved GRIN preform to make the GRIN fiber lenses, e.g., GRIN fiber lenses 18 of FIG. 2.

To form the GRIN preform, layers of silica-glass are deposited inside a silica-glass cladding tube by MCVD (step 102). During the MCVD, a time-varying partial pressure of dopant gases is bled into the gas mixture used to deposit silica-glass on the inside of the cladding tube. Exemplary dopants include Ge, Al, P, and F. Introduction of one or more of these dopants into the silica-glass changes the refractive index of the glass. The partial pressure of dopant gas is varied during the MCVD process to produce a non-trivial radial profile of dopant atoms in the final silica-glass preform.

The radial profile in dopant atoms produces a selected radially graded refractive index in the final preform. Exemplary profiles for the dopant density and the refractive index have profiles with concave downward or negative radial curvature. Often, the index profile varies as the square of the distance from the preform's axis in the core of the preform, e.g., profiles 27, 29 of FIGS. 3A and 3B. Other radial profiles may be obtained by suitably altering the time-variation of the partial pressure of dopant atoms during the MCVD. Non-quadratic profiles in GRIN fibers are capable of reshaping of light beams therein as is known to those of skill in the art.

The method 100 includes using the tube produced by the internal deposition to form the rod-like preform. To form the rod-like preform, heat is applied to partially collapse the tube of doped silica-glass (step 104). In one embodiment, the heating includes making repeated passes of the tube through a hot zone of a furnace. The heating is stopped prior to totally blocking the axial channel in the tube with glass.

After partially collapsing the tube, a silica-glass etchant mixture is passed through the axial channel to remove several layers of glass from the axis of the tube (step 106). An exemplary gaseous etchant mixture includes $C_2F_7$, $O_2$, and $Cl_2$. Other gaseous etchant mixtures include HF. The removed layers have lower dopant concentrations than adjacent outer layers of silica-glass, because dopants vaporize and are lost through the tube's axial canal during the heating used to collapse the tube. If these layers with lower dopant densities were not removed, the final preform would have an axial dip in dopant density and a corresponding axial dip in refractive index. The axial dip in refractive index interfered the operation of some conventional GRIN fiber lenses.

After the etching removal of several central layers of glass, the tube is externally heated to finish its collapse to a rod-like preform of doped silica glass (step 108).

After cooling the preform, etchants are applied to the outer surface to remove a selected thickness of cladding tube from the outside of the preform (step 110). Removing a portion of the cladding tube enables subsequent drawing of glass fibers with less or no cladding, e.g., see profiles 27 and 29 in FIGS. 3A and 3B. These thin-clad or non-clad fibers are advantageous for GRIN fiber lenses, because such fibers enable an optical beam to expand over a larger portion of the cross section of the final GRIN fiber. Spreading the beam over a larger cross section decreases the associated numerical aperture and decreases power densities so that defects on the end surface of the lens or on the target of the emitted beam are less likely to cause component damage.

Fabrication of GRIN fiber lenses also includes using a standard fiber drawing furnace to draw GRIN fiber from the graded-index preform (step 112). After cooling, one end of the drawn GRIN fiber is fused to one end of a standard fiber, i.e., a fiber with a non-graded index core (step 114). To fuse the GRIN and standard fibers, the ends of the two fibers are heated with an electrical arc or a tungsten filament in an argon environment while the ends are appropriately aligned and positioned adjacent each other.

Finally, the GRIN fiber is cleaved to produce an optical lens with a desired length (step 116). The final attached GRIN fiber lenses has a pitch of ¼, ½, or any other desired length and is fused to the fiber on which it functions as a beam collimator and expander.

To reduce reflections from the face of the final fiber device back into the fiber, the cleaving is often performed along a direction that is not perpendicular to the axis of the GRIN fiber. In a non-GRIN optical fiber, cleaving the fiber's end face at an 8 degree angle with respect to a direction perpendicular to the fiber's axis significantly reduces back reflections. For a GRIN fiber lens, this cleaving angle can be reduced to less than 8 degrees from a direction perpendicular to the lens axis to achieve the same reduction in back reflections into an attached optical fiber, e.g., a preferred cleave angle is about 0.5–2 degrees.

The method 100 produces GRIN fiber lenses, e.g. lens 18 of FIG. 2, that have lower refractive powers per unit length than conventional GRIN fiber lenses, e.g., lens 11 of FIG. 1. Thus, the new GRIN fiber lenses are significantly longer than conventional GRIN fiber lenses having the same optical power. The longer lenses collimate light better and are easier to manipulate during device construction. Exemplary GRIN fiber lenses with low radial dopant gradients have full pitch lengths of about 2, 3, or 4–20 mm.

The GRIN fiber lens 18 of FIG. 2 can also be made by vapor axial deposition (VAD), outer vapor deposition (OVD), and sol-gel processes that are known to those of skill in the art. Such processes are also able to avoid creating an axial dip in refractive index in the final GRIN fiber lens.

2. Fiber Devices That Use Grin Fiber Lenses

Various embodiments provide optical fiber devices that are described below. The various devices described can use either conventional GRIN fiber lenses, e.g., lens 11 of FIG. 1, or new GRIN fiber lenses, e.g., lens 18 of FIG. 2.

Figure 6A:
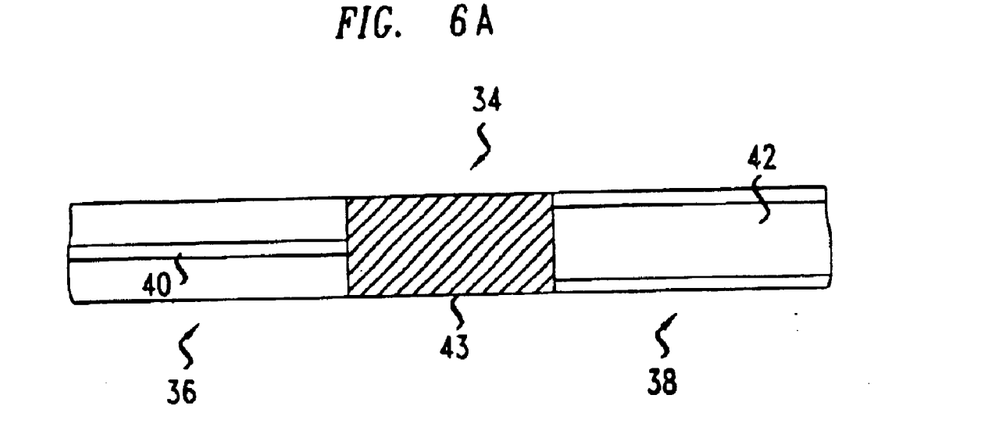
FIG. 6A is a cross-sectional view of a mode converter.

FIG. 6A shows a mode converter 40 that couples a pair of optical fibers 36, 38 having different fundamental or higher propagating modes. In some embodiments, the optical fibers 36, 38 have cores of different diameters or have refractive index jumps of different sizes across core-cladding boundaries. In the mode converter 40, GRIN fiber lens 43 is attached to the ends of the optical fibers 36, 38. In exemplary mode converters 40, the GRIN fiber lens 43 is either fused directly to the optical fibers 36, 38 or joined to the fibers 36, 38 by a glue layer (not shown) whose thickness is not greater than the width of the cores of fibers 36, 38.

Since optical fibers 36, 38 have different core diameters and/or refractive index jumps, the fibers 36, 38 have propagating modes, e.g., fundamental modes, with different sizes. Herein, the size of a propagating mode is defined as the mode's full-diameter between half-maximum amplitude values. Due to the different sizes of the propagating modes, coupling the optical fibers 36, 38 directly would produce a significant coupling loss of optical energy, i.e., a splice loss.

To reduce splice losses, GRIN fiber lens 43 is positioned between optical fibers 36, 38 and is selected to expand the narrower propagating mode of optical fiber 36 to have a larger diameter that equals that of the propagating mode of the optical fiber 38. Designing the GRIN fiber lens 43 to produce the appropriate size conversion entails selecting an appropriate lens length. One of skill in the art would know how to select the length of GRIN fiber lens 43 based the amount of magnification needed to convert the size of the propagating mode of one fiber 36 into that of the propagating mode of the other fiber 38.

In other embodiments, the mode converter 34 couples a waveguide other than an optical fiber to optical fiber 38.

Figure 6B:
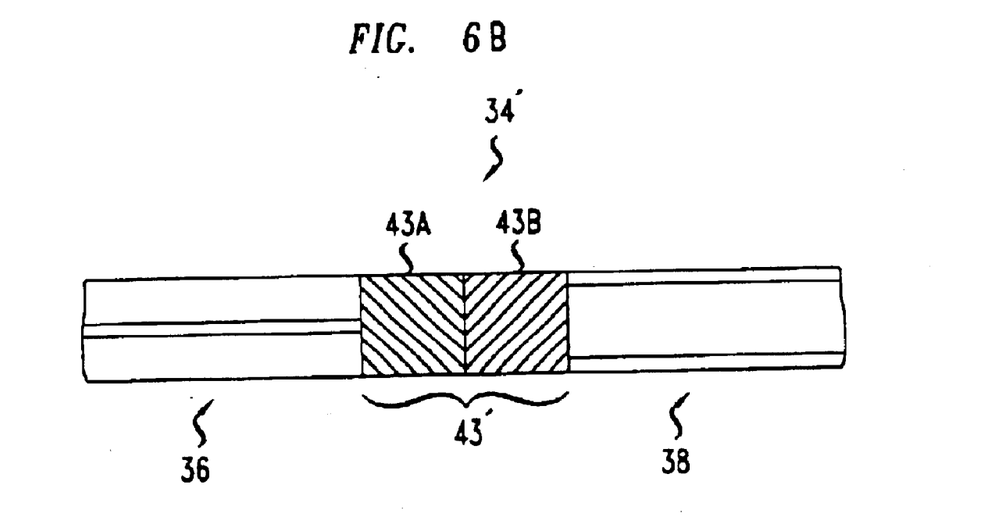
FIG. 6B is a cross-sectional view of a mode converter that uses a compound GRIN fiber lens.

FIG. 6B shows a specific embodiment 34' of the mode converter 34 of FIG. 6A. In the mode converter 34', GRIN fiber lens 43' is a compound lens made of a sequence of GRIN fiber lens elements 43A, 43B. The first element 43A is fused directly to the end of optical fiber 36, and the last element 43B is fused directly to the end of optical fiber 38. Exemplary GRIN elements 43A and 43B are fused together and have different refractive index profiles and lengths. The lengths and index profiles of the two lens elements 43A, 43B are selected to better optically couple the fibers 36, 38. In some embodiments, the first GRIN element 43A expands the light beam emitted by fiber 36, and the second element 43B focuses the beam waist to the size of the propagating mode in the fiber 38.

Figure 7A:
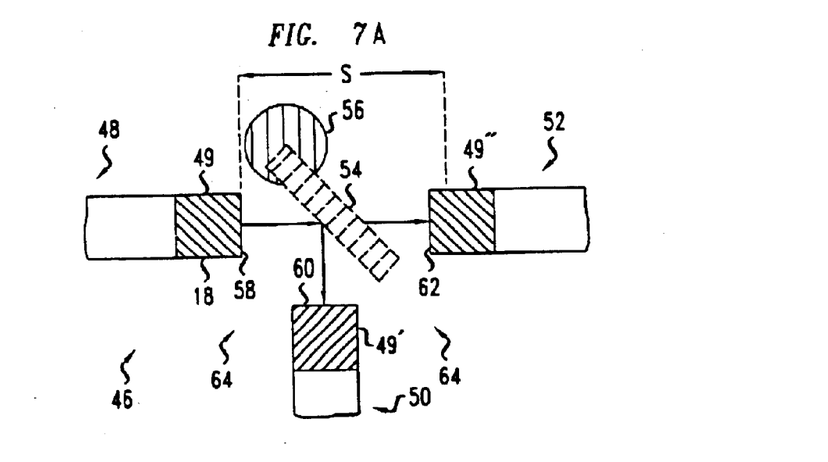
FIG. 7A is a top view of a 1×2 micro-optical router.

FIG. 7A shows a 1×2 micro-optical router 46. The router 46 includes an input optical fiber 48, output optical fibers 50, 52, and a movable reflector 54 for directing light from the input fiber 48 to a selected one of the output fibers 50, 52. The terminal ends of the optical fibers 48, 50, 52 are fused to GRIN fiber lenses 49, 49', 49", e.g., identical GRIN fiber lenses. The GRIN fiber lens 49 functions to collimate or focus the emitted light beam from fiber 48. The GRIN fiber lenses 49', 49" function to collect light and couple the collected light into the associated optical fibers 50, 52. The output optical fibers 50, 52 are located so that the waist of the beam emitted by the input optical fiber 48 is at the midpoint of the optical path between the input and output optical fibers 48, 50, 52. The reflecting surface of reflector 54 is located at the beam waist to within about a Rayleigh range when positioned to reflect light to the output optical fiber 50.

To select a routing, reflector 54 is moved in or out of the path of the light beam emitted by optical fiber 48. The reflector 54 is fixed to a micro-electro-mechanical (MEM) device 56 that moves the reflector 54 in and out of the beam's optical path in response to electrical signals applied to the MEM device 56.

The GRIN fiber lenses 49, 49', 49" improve beam collimation and collection so that terminal ends 58, 60, 62 can be separated by distances that are large enough to enable insertion and removal of reflector 54 in routing region 64. In embodiments of router 46 based on the new GRIN fiber lenses 18 of FIGS. 2, 3A–3B, and 4A, better beam collimation enables distances between terminal ends 58, 60, 62 to be as large as about 9 mm. For these large inter-fiber distances, the GRIN fiber lenses 49, 49', 49" reduce optical coupling losses to less than about 0.5 decibels (dB) and preferably to less than about 0.2 dB–0.05 dB. However, larger inter-fiber spaces involve more serious fiber device alignment issues.

In some embodiments, the micro-router 46 has an overall size, S, that is much smaller than the overall size of an analogous router in which the GRIN fiber lenses 49, 49', 49" are replaced by conventional lenses with curved refractive surfaces. The lenses with curved refractive surfaces have larger diameters than the GRIN fiber lenses 49, 49', 49". The larger lens diameters require positioning the ends of the input and output fibers at larger separations in such a router than in the micro-router 46. The lenses with curved refractive surfaces also typically produce larger diameter collimated beams in the routing region than the fused GRIN fiber lenses 49 of micro-router 46. The larger beam diameters necessitate a larger reflective surface on the routing reflector of the router whose lenses have curved refractive surfaces than would be needed on the reflector 56 of the micro-router 46.

In some embodiments of micro-router 46, the distance, S, characteristic of separations between GRIN lenses 49, 49', 49" has a value in the range of about 1–3 times the fiber diameter to about 1–3 times the Rayleigh range, e.g., less than about 1 mm. In these embodiments, the small size of the region 64 between the lenses 49, 49', 49" is achieved in part, because diameters of the attached GRIN fiber lenses 49, 49', 49" are small and in part, because the reflective surface on reflector 54 has a small beam acceptance window. The acceptance window for reflecting the input beam can be less than the fiber diameter, because the GRIN fiber lens 49 produces a beam waist that is smaller than the diameter of fiber 48. Both the small diameter GRIN fiber lenses 49, 49', 49" and the smallness of reflector 54 enable the router 46 to be much smaller than routers that use lenses with curved refractive surfaces.

Figure 7B:
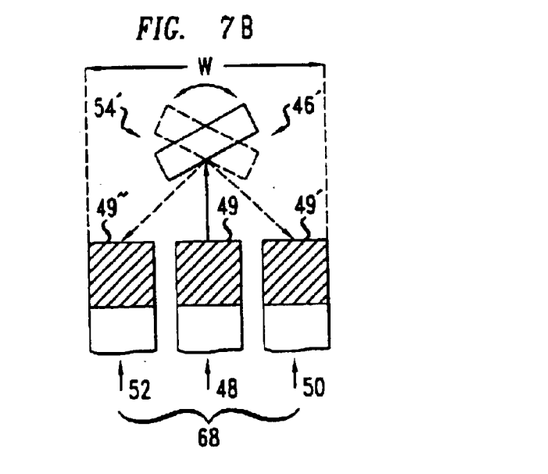
FIG. 7B is a top view of another topology for a 1×2 micro-optical router.

FIG. 7B shows an alternate embodiment 46' of the router 46 shown in FIG. 7A. In router 46', the fibers 48, 50, 52 are adjacent and located in a linear array 68. A single rotatable reflector 56', e.g., a MEMS controlled reflector, selectively routes light from the fiber 48 to either the fiber 50 or the fiber 52. In some embodiments, the axes the fibers 50 and 52 are slightly tilted with respect to the axis of the fiber 48 to insure that light from the reflector 56' parallel to the axis of the fibers 50, 52.

Arranging the fibers 48, 50, 52 in array 68 makes the width of the router 46' roughly equal to the width, W, of the array 68. The small diameters and fine collimation of GRIN fiber lenses 49, 49', 49" enable packing the fibers 48, 50, 52 closely in the array 68. Thus, embodiments of the router 46 can have a width, W, that is much smaller than the width of a similar-form router in which lenses with curved refractive surfaces replace the GRIN fiber lenses 49, 49', 49".

Figure 7C:
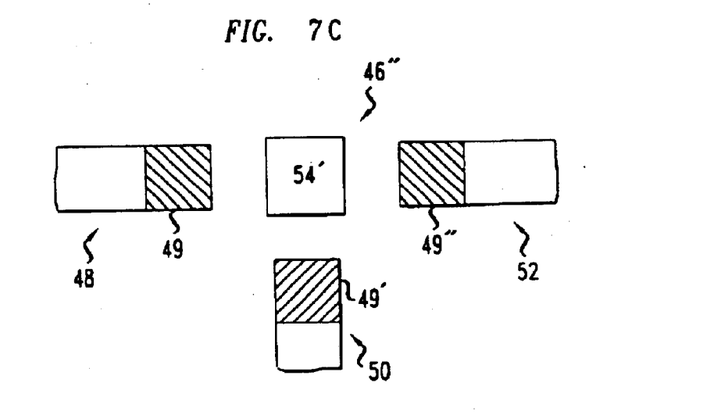
FIG. 7C is a top view of a device that optically couples three optical fibers.

FIG. 7C shows an embodiment of an optical device 46" that couples three optical fibers 48, 50, 52 based on light polarization, light wavelength, or relative fiber position. The optical fibers 48, 50, 52 have attached GRIN fiber lenses 49, 49', 49" that collimate and collect light. The device 46" includes an optical element 54' that transmits light between the optical fibers 48, 50, 52, e.g., in a manner that depends on polarization or wavelength. In various embodiments, optical device 54' includes a polarizing beamsplitter, a grating, an optical circulator, or a wavelength selective reflector such as a Bragg grating.

Figure 8:
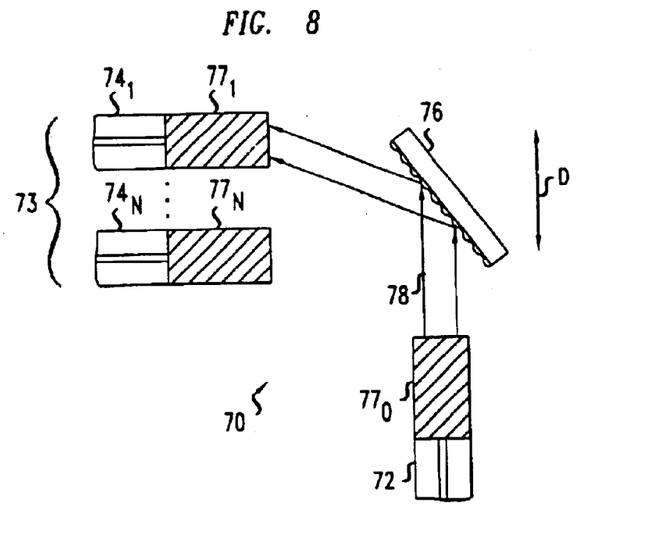
FIG. 8 is a cross-sectional view of a 1×N micro-optical router.

FIG. 8 shows a 1×N micro-optical router 70 that includes an input optical fiber 72, an output array 73 of N output optical fibers $74_1$–$74_N$, and a reflector 76. The optical fibers 72, $74_1$–$74_N$ are single-mode fibers to which terminal GRIN fiber lenses $77_0$–$77_N$ have been fused. The light beam 78 from the input optical fiber 72 intersects the reflector 76 near the waist of the beam 78, i.e., within ½ a Rayleigh range.

Exemplary reflectors 76 include mirrors that move or rotate and diffraction gratings that reflect light in a wavelength dependent manner. For example, the router may be a spectrally sensitive demultiplexer for a wavelength division multiplexed network.

The GRIN fiber lenses $77_0$–$77_N$ expand and collimate the light beam 78 of the input optical fiber 72 and focus the light beam 78 into the output optical fibers $74_1$–$74_N$. Due to the GRIN fiber lenses $77_0$–$77_N$, the output array 73 of optical fibers $74_1$–$74_N$ and input optical fiber 72 can be separated by an optical path that is long enough to enable insertion of bulk reflector 76 into the path without significant coupling losses. For the router 70 coupling losses are typically less than about 0.5 dB-0.2 dB and preferably less than about 0.1 dB.

In micro-optical router 70, GRIN fiber lens 770 focuses the beam from fiber 72 onto a reflective acceptance window on the reflector 76. Perpendicular to direction D, the diameter of the acceptance window is less than the fiber diameter. Also, the use of the GRIN fiber lenses $77_0$–$77_N$ enables an increased fiber packing density in the array 73 without interference between light beams reflected towards different ones of the fibers $74_1$–$74_N$. Finally, the use of GRIN fiber lens 770 enables the acceptance window and overall size of reflector 76 to be smaller than that of the reflector that would otherwise be needed in a router using lenses curved refractive surfaces (not shown). Thus, using the GRIN fiber lenses $77_0$–$77_N$ enables greater miniaturization in micro-router 70 than in a fiber router based on lenses with curved refractive surfaces.

Other embodiments use the GRIN fiber lens 18 of FIG. 2 to construct N×1 routers (not shown) by methods that would be obvious to one of skill in the art in light of the above-disclosure. For example, a 2×1 router can be constructed by exchanging designations of input and output for fibers 48, 50, 52 in 1×2 micro-router 46 of FIG. 7A.

Figure 9:
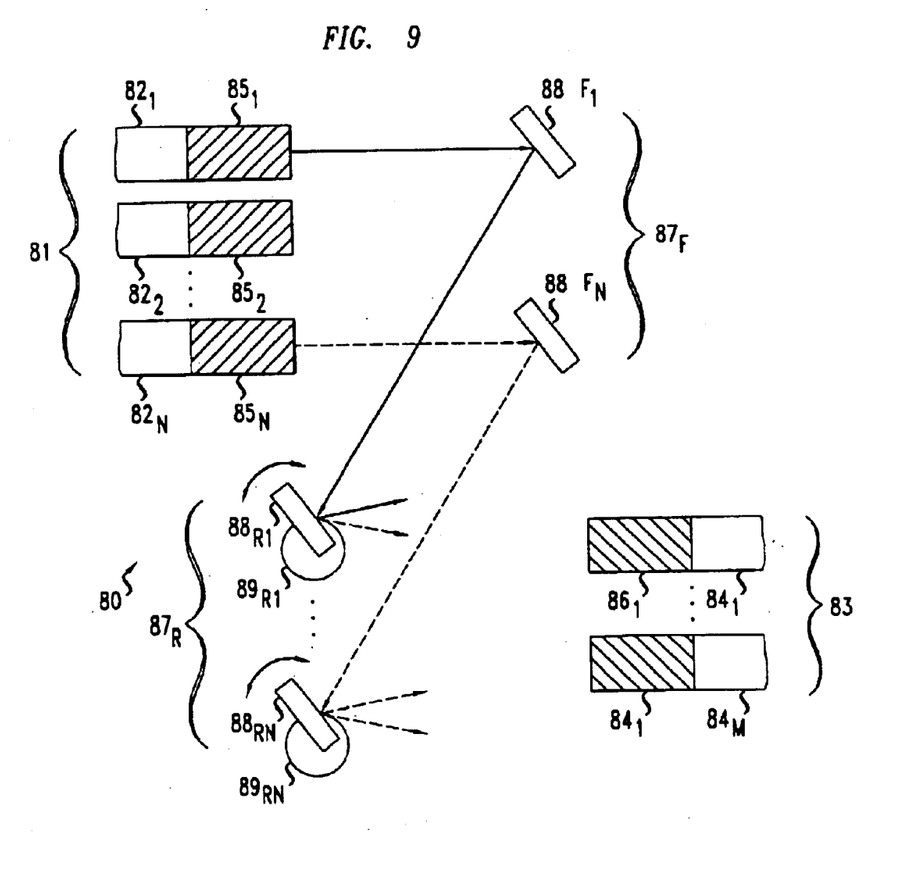
FIG. 9 is a top view of an N×M micro-optical router.

FIG. 9 is a top view of an N×M optical router 80. The router 90 includes an array 81 of N input optical fibers, $82_1$–$82_N$, and an array 83 of M output optical fibers, $84_1$–$84_M$. The fibers $82_1$–$82_N$, $84_1$–$84_M$ have GRIN fiber lenses $85_1$–$85_N$, $86_1$–$86_M$ fused to terminal ends thereof. The GRIN fiber lenses $85_1$–$85_N$, $86_1$–$86_M$ provide beam collimation and collection functions analogous those previously described in relation to GRIN fiber lenses 49, 49', 49" of FIG. 7A. Between the input and output fibers $82_1$–$82_N$, $84_1$–$84_M$ are banks $87_F$, $87_R$ of fixed and routing reflectors, $88_{F1}$–$88_{FN}$, $89_{R1}$–$89_{RN}$. Exemplary reflectors $89_{R1}$–$89_{RN}$ include wavelength-selective reflectors, e.g., gratings, and wavelength insensitive reflectors. Properly aligning the reflectors $88_{R1}$–$88_{RN}$ routes light from individual ones of the input fibers $82_1$–$82_N$ to selected ones of the output fibers, $84_1$–$84_M$. The reflectors $88_{R1}$–$88_{RN}$ are operated by MEMs devices $89_1$–$89_N$ and have acceptance windows for input beams whose diameters are smaller than the inter-fiber spacing, IFS, of array 81.

By using attached GRIN fiber lenses $85_1$–$85_N$, $86_1$–$86_M$ the fiber packing densities in the arrays 81, 83 can be increased above fiber packing densities of an N×M fiber router in which lenses with curved refractive surfaces (not shown) replace the GRIN fiber lenses $85_1$–$85_N$, $86_1$–$86_M$ of FIG. 9. Similarly, sizes of reflective surfaces of reflectors $88_{F1}$–$88_{FN}$, $89_{R1}$–$89_{RN}$ in the router 80 are smaller than sizes of reflective surfaces of reflectors in routers based on lenses with curved refractive surfaces, because the beam diameters produced by the GRIN fiber lenses $85_1$–$85_N$ are small. Both effects enable the new N×M to be smaller than an N×M router based on lenses with curved refractive surfaces.

Figure 10:
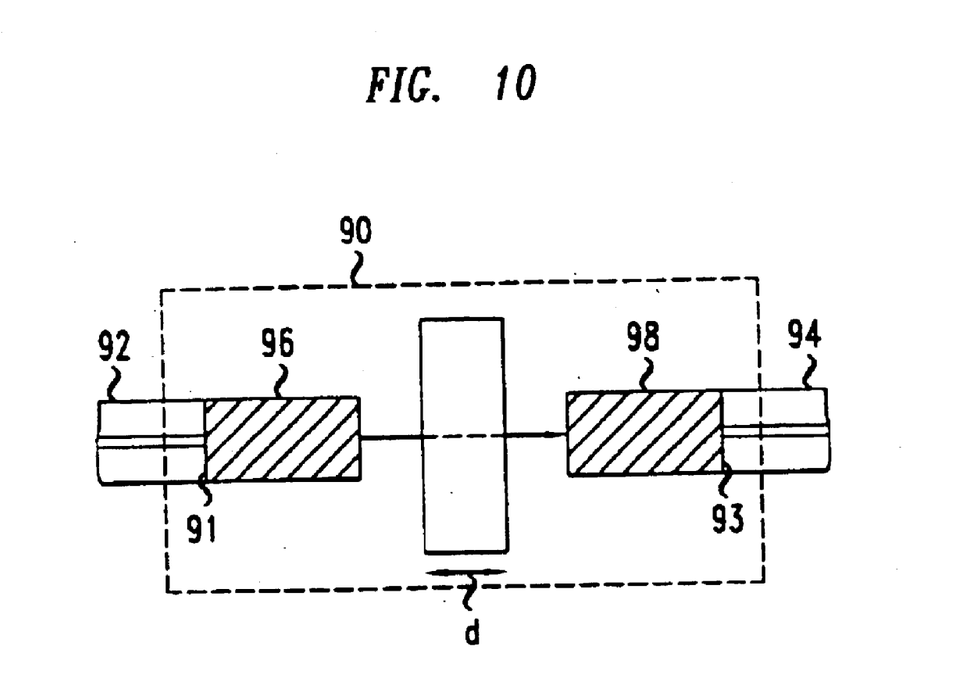
FIG. 10 is a cross-sectional view of an optical fiber with an in-line optical device.

FIG. 10 shows a micro-optical device 90 that is located in-line between ends 91, 93 of optical fibers 92, 94. Exemplary micro-optical devices 90 include wavelength-sensitive add/drop modules, polarizers, polarization rotators, one-way optical isolators, and controllable optical attenuators. The ends 91, 93 of the optical fibers 92, 94 are fused to GRIN fiber lenses 96, 98. The GRIN fiber lens 96 collimates light emitted by the optical fiber 92. The GRIN fiber lens 98 focuses received light into the optical fiber 94. The micro-optical device 90 has an approximate thickness, d, that is not greater than the Rayleigh range associated with the GRIN fiber lenses 96, 98. For such a thickness, the GRIN fiber lenses 96, 98 reduce diffraction-related coupling losses.

Other embodiments of the invention will be apparent to those skilled in the art in light of the specification, drawings, and claims of this application.

What is claimed is:

1. A method for fabricating a GRIN fiber, comprising:

forming a tube of silica-glass having a tubular core and a concentric tubular cladding adjacent and external to the tubular core, the core having a dopant density with a radially graded profile;

partially collapsing the tube by applying heat thereto, the partially collapsed tube having a central channel;

passing a glass etchant through the central canal to remove an internal layer of silica glass; and then, collapsing the etched tube to a rod-like perform; and drawing a GRIN fiber from the perform; and wherein the drawing produces a GRIN fiber whose core has a refractive index with a profile having a radial second derivative whose average magnitude is less than about $1.7 \times 10^{-6}$ microns$^{-2}$ times the value of the refractive index on the axis of the GRIN fiber lens.

2. The method of claim 1, wherein said average magnitude is less than about $0.9 \times 10^{-6}$ microns$^{-2}$ times the value of the refractive index on the axis of the GRIN fiber lens.

3. The method of claim 1, wherein the forming further comprises:

depositing a portion of the core on an inside surface of the tubular cladding, the depositing including introducing a mixture of a precursor for dopant deposition and a precursor for silica-glass deposition inside the tubular cladding, the depositing including varying the percentage of the precursor for dopant in the mixture with time.

4. The method of claim 3, further comprising:

removing at least an outer layer of the tubular cladding tube from the preform.

5. The method of claim 1, further comprising:

fusing a portion of the GRIN fiber to another optical fiber.

6. The method of claim 5, further comprising:

cleaving the fused GRIN fiber to form a GRIN fiber lens with a length of at least 2 millimeters.

7. The method of claim 5, further comprising:

cleaving the fused GRIN fiber to form a GRIN fiber lens with an end face whose normal is not parallel to the axis of the GRIN fiber lens.

8. The method of claim 1, wherein said magnitude is less than about $5.0 \times 10^{-7}$ microns$^{-2}$ times the value of the refractive index on the axis of the GRIN fiber lens.

9. The method of claim 1, further comprising:

etching the preform to remove an outer layer of the tubular cladding.

* * * * *